United States Patent [19]
Misra

[11] Patent Number: 6,012,586
[45] Date of Patent: Jan. 11, 2000

[54] MEDICAL PROCEDURE KIT

[75] Inventor: Vijay K. Misra, Brentwood, Tenn.

[73] Assignee: Maxxim Medical, Inc., Clearwater, Fla.

[21] Appl. No.: 08/976,617

[22] Filed: Nov. 24, 1997

[51] Int. Cl.[7] .............................. B65D 69/00; A61B 17/06
[52] U.S. Cl. .................... 206/571; 206/370; 206/438; 206/564; 220/DIG. 6
[58] Field of Search .................... 206/561–564, 206/363, 364, 370, 372, 373, 570–572, 438, 204; 220/DIG. 6

[56] References Cited

U.S. PATENT DOCUMENTS

| | | | |
|---|---|---|---|
| 3,250,283 | 5/1966 | Reinfeld | 206/561 X |
| 3,329,261 | 7/1967 | Serany, Jr. et al. | 206/364 X |
| 3,713,529 | 1/1973 | Meksula | 206/373 X |
| 3,807,954 | 4/1974 | McDonald | 206/563 X |
| 3,851,649 | 12/1974 | Villari | 206/438 |
| 4,046,254 | 9/1977 | Kramer . | |
| 4,053,280 | 10/1977 | Salisbury | 206/363 |
| 4,085,987 | 4/1978 | Vartdal | 220/DIG. 6 |
| 4,128,173 | 12/1978 | Lazarus et al. . | |
| 4,153,160 | 5/1979 | Leigh | 206/370 |
| 4,266,669 | 5/1981 | Watson . | |
| 4,595,102 | 6/1986 | Cianci et al. . | |
| 4,752,453 | 6/1988 | Nichols | 206/438 X |
| 4,886,165 | 12/1989 | Annett . | |
| 4,898,276 | 2/1990 | Georgakis | 206/370 X |
| 4,928,830 | 5/1990 | Brewer . | |
| 4,938,355 | 7/1990 | Rocco | 206/372 |
| 4,955,878 | 9/1990 | See et al. . | |
| 5,031,768 | 7/1991 | Fischer . | |
| 5,031,775 | 7/1991 | Kane | 206/571 |
| 5,174,453 | 12/1992 | Stoeffler . | |
| 5,281,400 | 1/1994 | Berry, Jr. . | |
| 5,339,955 | 8/1994 | Horan et al. | 206/370 |
| 5,353,929 | 10/1994 | Foster | 206/364 |
| 5,366,071 | 11/1994 | Laszlo | 206/373 X |
| 5,586,163 | 12/1996 | Goldstein . | |

*Primary Examiner*—Bryon P. Gehman
*Attorney, Agent, or Firm*—Kenneth M. Bush; Veal & Bush, LLC

[57] ABSTRACT

The present invention is directed to a medical procedure kit for performing an angiographic or other medical procedure. The kit comprises a housing having a central compartment and two side compartments that can be filled with supplies and folded over the central compartment to form a sealed kit for shipment and storage. A shelf is supported in the central compartment and includes a number of wells for holding various medical instruments and supplies needed for the particular procedure and also has a sloped surface leading toward a drain hole for draining waste fluids from the shelf and into the central compartment. When a procedure is complete, the used equipment is placed into the housing and the housing is closed, sealed in a plastic bag, and discarded.

20 Claims, 5 Drawing Sheets

MEDICAL PROCEDURE KIT

The present invention is directed toward a medical procedure kit, and more specifically, towards a medical procedure tray and kit that includes equipment and preparations useful for performing a given medical procedure.

BACKGROUND OF THE INVENTION

Before a given medical procedure can be performed, it is necessary to assemble all of the instruments, supplies, drugs, and other preparations that are likely to be needed for the procedure and arrange them on or near a procedure tray so that they are accessible to the doctor or technician performing the procedure. Because it can be difficult to locate additional equipment once a procedure has started, especially when an emergency situation arises, items must be provided even if there is only a small chance that they will be needed. Furthermore, different procedures require different combinations of instruments and drugs, and it can be time consuming for a nurse or technician to determine whether the proper combination has been supplied in any given instance.

After equipment has been provided and arranged for use, it must all be kept clean, and many instruments must also be kept sterile. If the equipment is laid out too far in advance of the commencement of a procedure, the chance of someone breaking sterility increases, and then contaminated items must be replaced with sterile items. It is therefore desirable to prepare for a procedure as close to the time of the procedure as possible. However, because it takes time to locate and assemble all of the necessary equipment, and because the schedules of persons preparing for and performing the procedure can vary, it is often not possible to do the preparation work as close to the start time for the procedure as desirable.

Once a procedure commences, care must be taken to keep blood and other bodily fluids from contaminating unused equipment. It is also important to keep items arranged in a logical manner so that the person performing the procedure, or his assistant, will be able to locate the items quickly. Awkwardly sized implements, such as catheters and the guide wires used in angiographic procedures, must be carefully monitored to prevent them from touching non-sterile surfaces, knocking over containers, pushing other instruments off of a work surface, or getting bent or tangled with themselves or other equipment. The efforts and attention of persons assisting in the procedure must remain focused on these objectives while at the same time trying to provide the support required by the physician. This requires that the attention of assistants be divided in a less than ideal manner.

A large number of towels, needles, gowns, drapes and other materials will become contaminated during any given procedure. These items must be disposed of properly either during the procedure or immediately thereafter. Needles and other sharps must be placed in a suitable protective container to prevent them from injuring persons coming in contact with the waste, gowns and drapes must be laundered or disposed of in a manner that protects persons handling the waste, and instruments used during the procedure must either be cleaned and sterilized or discarded. Again, this is a time consuming process, and one which requires thought on the part of those involved to ensure that all medical waste finds its way to the appropriate receptacle. A lapse in concentration could result in persons unknowingly being exposed to dangerous medical waste.

Furthermore, the nature and number of instruments, and the amounts of various preparations used must be monitored so that a patient can accurately be charged. The large number of items required for any given procedure complicates this accounting procedure, and furthermore, occupies the time of medical personnel that could better be used to provide patient care. It would therefore be desirable to provide a kit, priced as a single unit, for containing all of the equipment and supplies necessary for performing a given procedure in a manner that allows for rapid set up and clean up, and which helps to organize the materials during a procedure while minimizing contamination between sterile and non-sterile objects.

SUMMARY OF THE INVENTION

These and other problems are addressed by the present invention which comprises a medical procedure kit for holding medical equipment and supplies in a logical fashion. The kit may be assembled using supplies from a hospital supply room, or it may be sold as a ready-to-use kit complete with substantially all of the items needed for performing a given procedure. Furthermore, the kit is compact, can be easily stacked and stored prior to use, and can be filled with used materials after a procedure is complete and disposed of as a single unit.

In a preferred embodiment, the kit comprises an outer housing that includes three compartments: a central compartment, and two side compartments attached to opposite sides of the central compartment by hinges. A shelf or tray is supported within the central compartment and includes a number of wells for holding various solid and liquid items. The wells on the shelf are filled with sealed containers of various drugs and preparations, other supplies and instruments such as gauze and hemostats are packed on top of the shelf, and the side compartments are folded up and over the center compartment and shelf to seal all of the supplies and equipment within the outer housing. This kit formed in this manner is easy to ship and store, and when it is needed for a procedure, it can be quickly located and placed on a suitable surface near the site of the medical procedure. The person preparing for the procedure knows ahead of time what is contained in the kit, and this eliminates much of the last minute searching for extra items. Therefore, the kit can be set up quickly, and the setup can be done closer to the time of the actual procedure than was practicable when each drug and instrument had to be supplied individually. Furthermore, the kit is sold at a given price. This simplifies accounting in that patients can be charged one price for the use of one kit, rather than for dozens or even hundreds of different items.

The kit can be place behind the physician where instruments are normally laid out, but beneficially, can also be placed on the table supporting a patient in front of the physician. Such placement provides easier access to the equipment in the kit during a procedure and eliminates the need to turn around to select other instruments during a procedure. Not only is this arrangement often more convenient for the person performing a procedure, but it is also safer. This is because when the physician turns around to return a needle or scalpel to the kit there is always a small chance that a bystander will be stuck or cut. Having the kit in front of the physician eliminates this problem.

During a procedure, a physician can easily locate and select the materials that he needs from the procedure kit. Because the wells are fixed with respect to the tray, items placed in certain wells will be easy to locate. Furthermore, the surface of the tray is sloped toward a drain opening so that blood or other bodily fluid that runs off of instruments and onto the tray will drain into the portion of the housing beneath the tray where it is contained by an absorbent material. Clamps can also be secured to the tray and housing to hold long instruments such as catheters and wires out of the way of other instruments where they are protected and easy to reach. When the procedure is complete, the disposable instruments from the tray are returned the kit along with sponges, wipes and other contaminated materials, the outer housing is closed and sealed over these contaminated items, and the unit is discarded. Providing a single housing for containing these items makes for a safer disposal and reduces the likelihood that persons will be exposed to any of the contaminated materials produced during a procedure.

It is therefore a principal object of the present invention to provide an improved medical kit for use during a medical procedure.

It is another object of the present invention to provide a kit for performing a medical procedure which kit includes a procedure tray.

It is a further object of the present invention to provide a kit for performing a medical procedure which kit has a procedure tray housed therein which can be used during the medical procedure.

It is still another object of the present invention to provide a procedure tray that includes a sloped surface and a drain hole for draining fluids from the surface of the tray.

It is still a further object of the present invention to provide a disposable medical procedure kit.

It is yet another object of the present invention to provide a kit for performing an angiographic procedure.

It is yet a further object of the present invention to provide a kit which can be placed on a procedure table in front of a physician during use.

BRIEF DESCRIPTION OF THE DRAWINGS

These and other objects of the invention will become apparent from a reading and understanding of the following detailed description of a preferred embodiment of the subject invention together hollowing drawings of which.

DETAILED DESCRIPTION OF A PREFERRED EMBODIMENT

Figure 1:
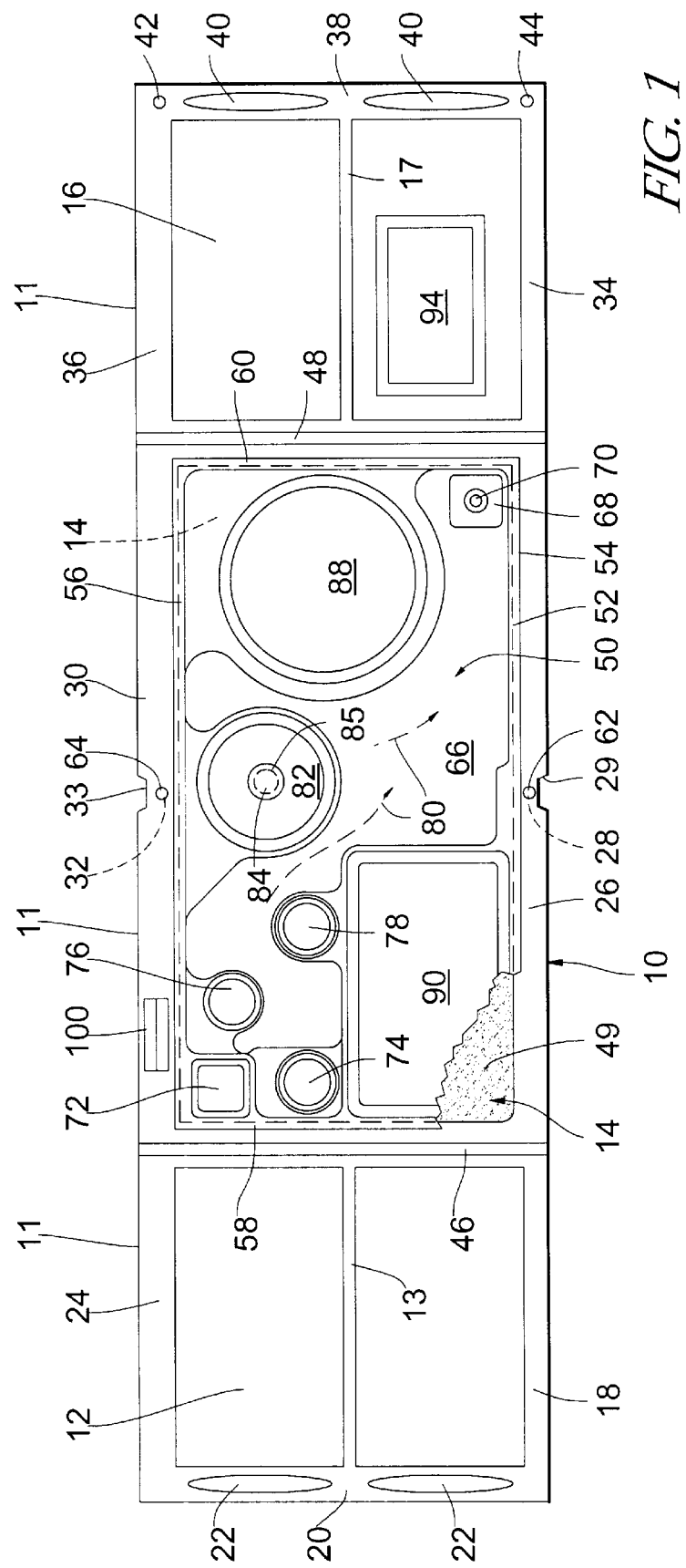
FIG. 1 is a plan view of a medical procedure kit according to the present invention.
Figure 2:
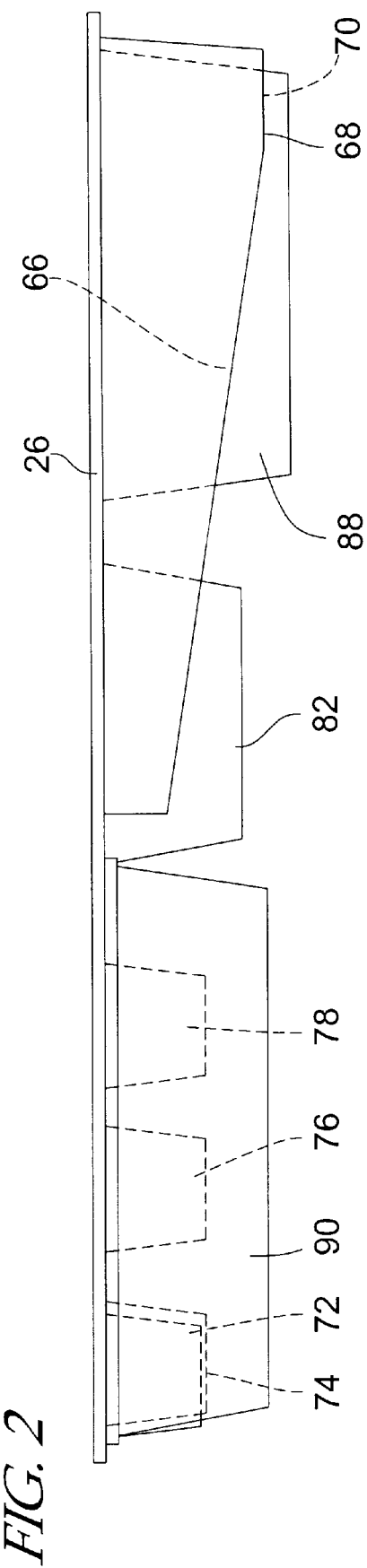
FIG. 2 is a front elevational view of the shelf that sits within the central compartment of the kit shown in FIG. 1.
Figure 3:
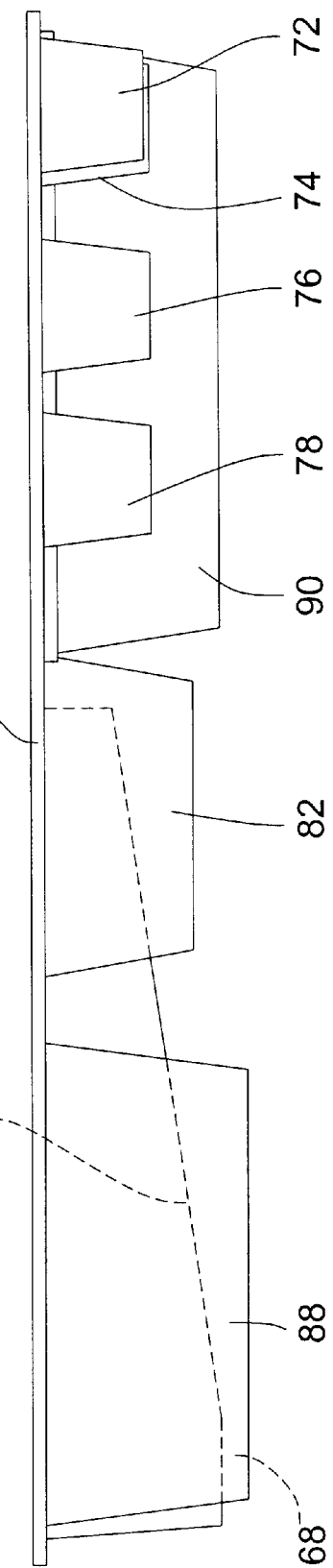
FIG. 3 a rear elevational view of the shelf shown in FIG. 2.
Figure 4:
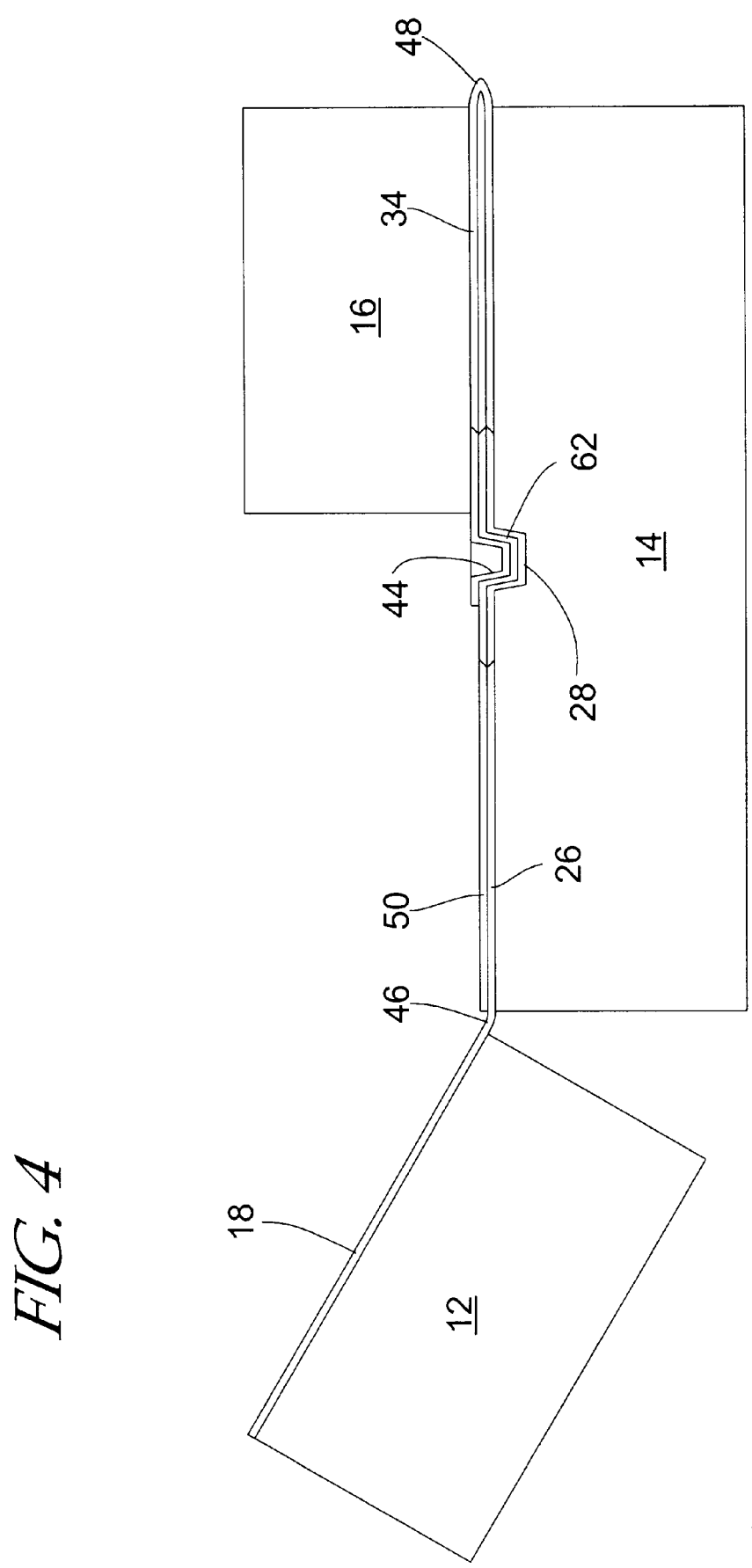
FIG. 4 is a front elevational view of the kit shown in FIG. 1 showing one of the side compartments of the tray folded over the central compartment.

Referring now to the drawings, wherein the showings are for purposes of illustrating a preferred embodiment of the subject invention only, and not for purposes of limiting same, FIG. 1 shows a medical procedure kit designated generally by the numeral 10 which kit includes an outer housing 11 having a first side compartment 12 with a central divider 13, a central compartment 14 and a second side compartment 16 with a central divider 17, each of which compartments is surrounded by a number of flanges. First side compartment 12 includes a front flange 18, a side flange 20 having a pair of indentations 22, and a rear flange 24; central compartment 14 includes a front flange 26 having a centrally located indentation 28 and notch 29, and a rear flange 30 having a centrally located indentation 32 and notch 33; and second side compartment 16 includes a front flange 34, a rear flange 36 and a side flange 38 having a pair of indentations 40. Second side compartment 16 further includes a first knob 42 extending from the junction of flanges 36 and 38 and a second knob 44 extending from the junction of flanges 34 and 38. These knobs extend toward the viewer as seen in FIG. 1. A first flexible land portion 46 connects side compartment 12 to central compartment 14, and a second flexible land portion 48 connects side compartment 16 to central compartment 14. The knobs and indentations serve to secure the side compartments to the central compartment for storage and disposal as will be described in detail hereinafter. Additional handles and similar elements can also be provided to allow a user to grip the kit more easily while it is being opened. Notches 29 and 33 make the kit easier to open. Furthermore, the bottom of central compartment 14 is coated with an absorbent gel 49 or other material for retaining waste liquids that enter compartment 14 during the course of a procedure.

Kit 10 includes a shelf or tray 50 having a lip 52 which lip includes a front portion 54, a rear portion 56, a first side portion 58 and a second side portion 60. Lip 52 overlies the front and rear flanges of central compartment 14 and land portions 46 and 48 to support shelf 50 over central compartment 14. Front portion 54 of lip 52 includes a centrally located depression 62 which fits within indentation 28 on central compartment front flange 26 and rear portion 56 of lip 52 similarly includes a depression 64 which fits within indentation 32 on central compartment rear flange 30. The seating of the depressions within the indentations helps to fix the tray with respect to the central compartment of the outer housing. In addition, lip 52 is preferably fastened over the central compartment such as by gluing or heat sealing to form a water-tight seal between the shelf and the outer housing.

Shelf 50 includes a sloped surface 66 which slopes generally downwardly in the direction from the rear to the front and from the left to the right as seen in FIG. 1 toward a drain 68 which includes an opening 70 extending through tray 50 and into the interior of central compartment 14. A number of wells are located in the shelf for holding a variety of different drugs, preparations, and instruments for performing a particular procedure. The kit shown in the preferred embodiment is intended for use during an angiographic procedure, and therefore will be described in terms of such a procedure. It should be understood, however, that a different arrangement and number of wells could be used for different procedures depending on the number and type of different materials needed for such a procedure.

Figure 5:
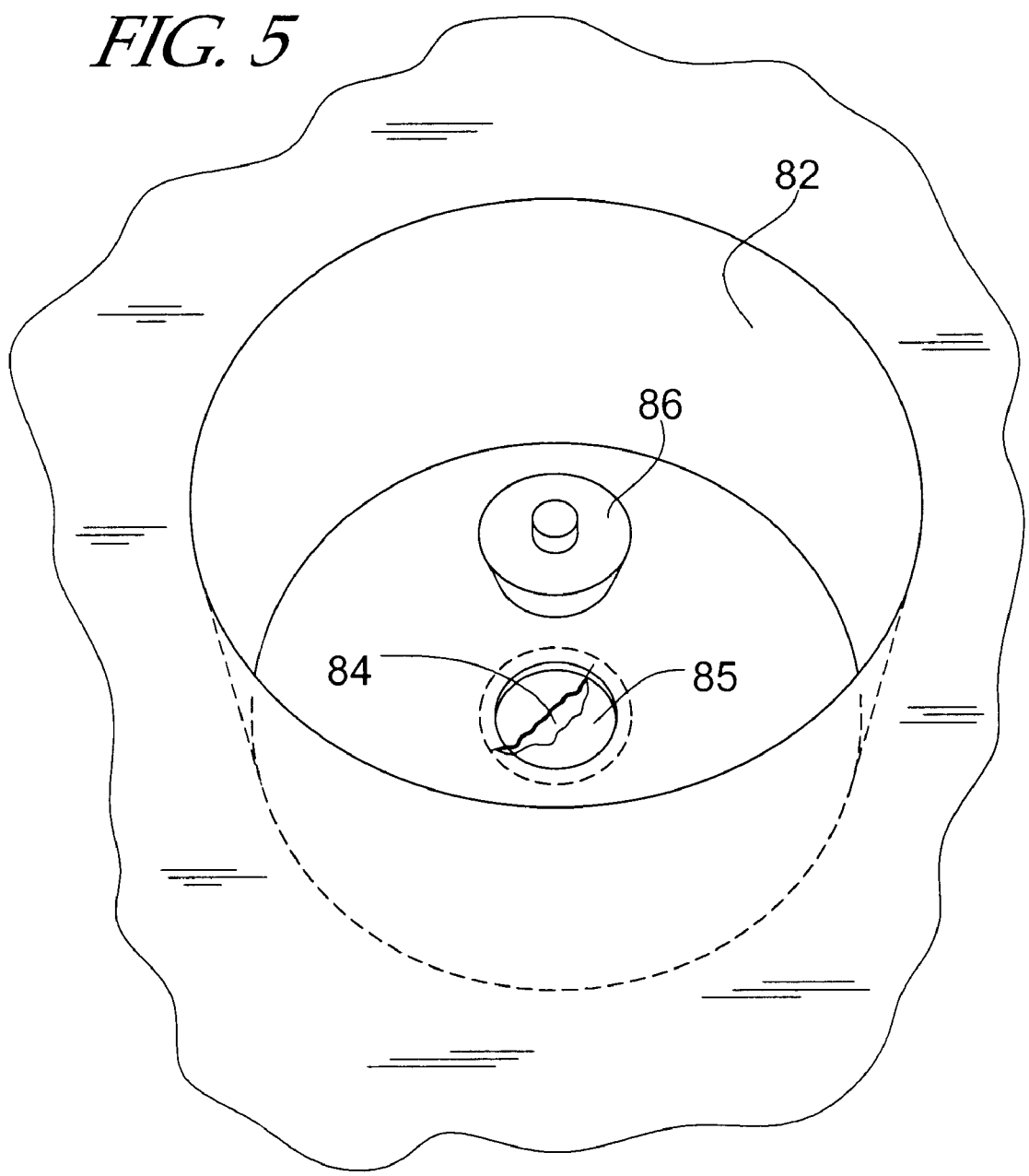
FIG. 5 is a perspective view of one of the wells from the shelf of FIG. 2 showing a plug being inserted into an opening at the bottom of the well.

Shelf 50 includes a first well 72 for holding a sponge or similar material into which used needles and other sharps can be inserted for safe keeping during the procedure. Three small wells 74, 76 and 78 are provided for holding containers of drugs such as lidocaine, heparin, and nitroglycerin. The drugs may be placed directly in the wells, but are preferably provided in separate sealed cups (not shown) which rest within each of the wells. This simplifies the manufacture and assembly of the kit and allows different drugs to be used when needed. The top openings of each well are raised above surface 66 to prevent liquids spilled on surface 66 from running into the wells. Instead, any such spilled liquid will run down surface 66 in the direction of arrows 80 toward drain 68, and from there, it will drop into central compartment 14 of outer housing 11 wherein it will be absorbed by absorbent material 49. A medium size well 82 is also provided, and this well is useful for storing a saline or saline and heparin solution for use during a procedure. This medium well 82 includes a rupturable bottom portion 84, as shown in FIG. 5, comprising a membrane 85 of plastic or similar material. Liquid is placed in well 82 during a procedure and it may become necessary to empty this liquid during the course of performing the procedure. To do so, rupturable portion 84 is pierced with a knife or other sharp instrument to allow any liquid contained in the well to drain into the interior of central compartment 14 of housing 11. A plug 86 is provided with kit 10 which fits within the opening left when the bottom of well 82 is ruptured and plug 86 can be inserted into the hole to once again make well 82 watertight. Similar rupturable portions can be provided in other wells if desired.

Figure 6:
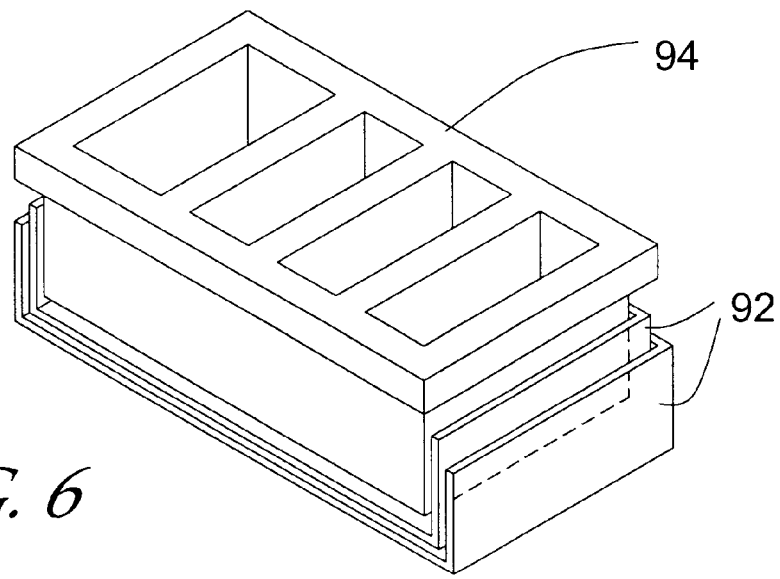
FIG. 6 is a perspective view of a removable insert that can be placed into one of the wells of the tray of the subject invention.

A large well 88 serves to hold catheter wires in neat coils so that they do not become tangled or contaminated. Finally, a large rectangular compartment 90 is provided for holding a number of nested inserts 92 and a subdivided insert 94 as shown in FIG. 6. The inserts are stacked inside one another with subdivided insert 94 placed on top. This stack of inserts fits securely within well 90 for storage.

First side compartment 12 of the outer housing is used to store gowns, drapes, or other large items during shipping. Second side compartment 16 is used to store miscellaneous items such as balloons, wires, stents, inflation devices, etc. Preferably, these compartments are provided with plastic covers for holding the materials therein in place during shipping and these covers are held in place with a removable adhesive or Velcro brand fastening material. After the items are removed from side compartments 12 and 16, inserts 92 are arranged in these now-empty compartments and used to hold a variety of different solid and liquid items. For example, one of the inserts 92 may be used to hold saline solution for glove washing during the procedure. Others may be used to hold supplies of wet and dry gauze. The dividers 13 and 17 in compartments 12 and 16 serve to limit the movement of these inserts within the side compartments and the compartments may be provided with a small lip if desired in order to better hold the removable inserts in place. Subdivided compartment 94 may be returned to well 90 or placed in one of the side compartments and used to hold and organize a number of small items such as syringes.

Figure 7:
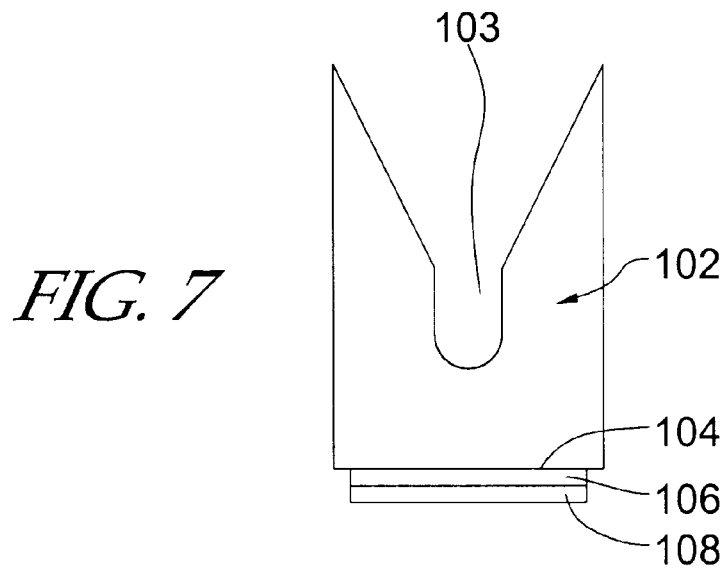
FIG. 7 is an end elevational view of a first type of clamp for use in connection with the subject kit; and, FIG. 8 is a sectional view of a second type of clamp for use in connection with the subject kit.
Figure 8:
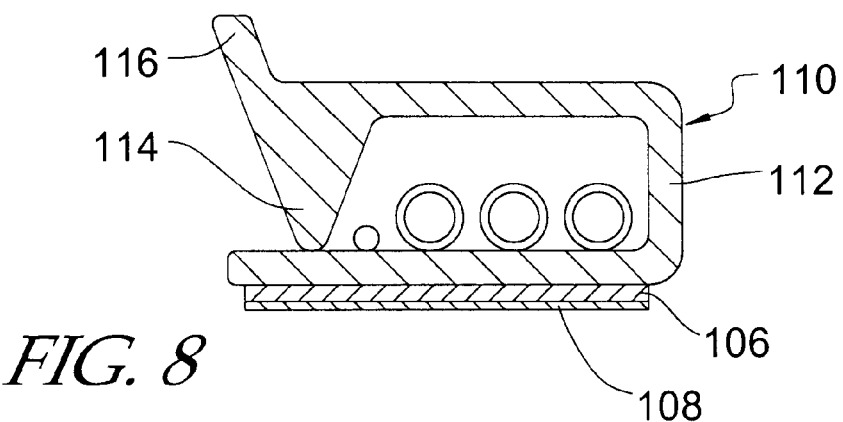

Kit 10 is also provided with a number of clamps or clips 100 for holding long items such as the catheters and wires used in angiographic procedures. Clips 100 may take many different forms, two of which are shown in FIGS. 7 and 8. FIG. 7 shows a V-shaped clip 102 which includes a V-shaped channel portion 103 and a flat bottom portion 104 coated with an adhesive 106. The adhesive is protected with a waxed paper 108, for example, in a well known manner, and paper 108 is easily removed from the adhesive to allow the clip to be fastened onto a suitable surface. The adhesive may comprise a short section of two-sided tape, for example. To use install the clips, paper 108 is removed therefrom and the clips are pressed against rear portion 56 of shelf lip 50 and rear flanges 24 and 36 of side compartments 12 and 16 respectively. Additional clips can be placed on side flanges 20 and 38 of the side compartments to accommodate the long flexible wires and catheters. These clips serve to hold the wires and catheters in position away from the other materials being used by the physicians or surgeons while at the same time leaving them readily accessible.

A second type of clip 110 is shown in FIG. 8. This clip comprises a generally C-shaped piece 112 of flexible material, such as any suitable plastic, and includes a triangular closure portion 114 which closes the open portion of the "C." These clips are each provided with an adhesive portion on their bottom walls, and a number of these clips are adhered to the rear lip and flanges of the kit as described above. An extension 116 on triangular portion 114 serves as a lever to allow closure portion 114 to be moved away from C-shaped piece 112 to allow catheters and wires to be inserted into the interior of the "C." The C-shaped portion springs back to its closed position with triangular portion 114 resting against the C-shaped portion when lever 116 is released. These clamps can be opened to remove a wire or catheter when needed. Alternately, the wires or catheters can be removed by pulling them through the clamps individually without opening the clamps since the clamps do not prevent the longitudinal movement of the objects held therein. Like clamps 102, clamps 110 are provided with the kit and can be fastened to the kit during the set-up prior to the procedure. It will also be appreciated that other types of clamps could be used and that these clamps could be fastened to the kit as part of the assembly process or even be formed as a part of the kit itself without exceeding the scope of this invention.

While the kit can be sold on its own and can be filled by hospital staff prior to a procedure, it is preferred that the kit be pre-filled with substantially all of the materials needed for a particular procedure, sealed, and shipped to hospitals and labs as a complete kit. The kit is assembled by taking an outer housing 11 and attaching a sponge or other absorbent material such as a gel to the bottom of the central compartment. Shelf 50 is then placed into central compartment 14 so that depressions 62 and 64 of the shelf rest in indentations 28 and 32 respectively of flanges 26 and 30. The indentations and depressions may be configured such that the shelf snaps securely into place and becomes difficult to remove. Preferably, the shelf is also heat sealed or glued to the central compartment to form a watertight seal therebetween. Next, sealed containers of lidocaine, heparin, and nitroglycerin are placed into small wells 74, 76, and 78, gowns, drapes, prep pads, gauze and towels are loaded into the side containers, catheter wires are coiled and placed into large well 88, and hemostats, needles, catheters and other materials are placed into any other available spaces. Plastic covers are then sealed over these side compartments to hold the contents thereof in place during shipping. Side compartment 16 is then folded about land 48 until front and rear flanges 34 and 36 overlie front and rear portions of tray lip 52. Knobs 42, 44 on the side compartment flange fit into depressions 64, 62 on tray 50 and help to hold side compartment 16 firmly against tray 50. Side compartment 12 is folded about land 46 in a similar manner until front and rear flanges 18 and 24 overlie front and rear portions 54 and 56 of tray lip 52. Indentations 22 on side flange 20 of compartment 12 fit over the upwardly extending bottoms of indentations 40 on side flange 38 of side compartment 16, and kit 10 can be sealed shut by pressing side flanges 20 and 38 firmly together. The entire kit is then sealed in an airtight plastic wrapper (not shown) to keep the materials therein sterile. Significantly, because central compartment 14 is longer than the side compartments, long objects such as catheters can be easily stored in the kit even in its folded configuration without excessive bending or coiling. In this configuration, having dimensions of about 24 inches by 24 inches by 6 inches, the kit can be easily stacked, shipped, and stored.

To use a kit, it is taken from storage and the outer wrap is removed. Side compartments 12 and 16 are unfolded and the gowns, drapes and other materials are removed or arranged in the kit as needed for the particular procedure. The clips are then placed around the outer lip and flanges as described above and the catheters and wires are placed in the clips. During the procedure, the various drugs and instruments are used, and any blood or other fluid that runs off of the instruments as they are returned to the tray runs down sloped surface 66 into drain 68 and through opening 70 into compartment 14. Excess saline and other solutions can also be poured into the drain, or the various wells can be emptied by rupturing their bottom walls. After the procedure is complete, the instruments, gowns, and preparations are all placed into the kit and the side compartments are folded over the central compartment as heretofore described. While the kit can be made to seal very tightly, it is preferable to provide a disposal bag into which the used kit can be placed to ensure that no fluids escape from the tray. The bag and kit are then disposed of along with other medical waste. Making the entire kit disposable eliminates the need to separate, clean and sterilize the materials used during the procedure and simplifies and makes safer the clean-up after the procedure is over.

The subject invention has been described herein in terms of a preferred embodiment, it being understood that obvious additions and modifications to this embodiment will become apparent to a person skilled in the relevant art upon a reading and understanding of this document. For example, the kit has been described in a configuration useful in connection with angiographic procedures, but could easily be modified so that it could be used for other medical or even veterinary procedures. All such obvious modifications are intended to be included within the scope of this invention to the extent that they are defined by the claims appended hereto.

I claim:

1. A medical procedure kit for performing a medical procedure, comprising:
   a. an impermeable housing having a top edge defining a top opening; and
   b. a procedure tray for holding medical supplies for use during the medical procedure having a top surface supported in said top opening of said housing in sealing engagement with said top edge, wherein said tray comprises a drain hole for allowing fluids to pass from said top surface into said housing and a recessed portion formed therein wherein said recessed portion comprises an opening in the bottom thereof for connecting said recessed portion to said housing and a rupturable membrane sealably covering said opening, wherein said rupturable membrane can be ruptured to void any fluids from said recessed portion into said housing.

2. A medical procedure kit according to claim 1 wherein at least a portion of said top surface of said procedure tray is sloped toward said drain hole to promote drainage of fluids from said top surface into said housing.

3. A medical procedure kit according to claim 1 further comprising at least one compartment depending from said procedure tray into said housing, wherein said at least one compartment comprises lips formed along the upper periphery thereof to prevent fluids on said top surface from entering said at least one compartment.

4. A medical procedure kit according to claim 1 further comprising at least one closure hingedly connected to said housing for covering said procedure tray and sealing said housing.

5. A medical procedure kit according to claim 1 further comprising a plug for sealing said opening after said rupturable membrane has been ruptured.

6. A medical procedure kit for performing a medical procedure comprising:
   a. an outer housing including a central compartment having a top edge defining a top opening and first and second side compartments hingedly connected to said central compartment, each of said side compartments having a top edge defining a top opening;
   b. a shelf supported in said central compartment top opening for holding medical supplies for use during the medical procedure, said shelf comprising at least one recessed portion formed therein wherein said recessed portion comprises an opening in the bottom thereof for connecting said recessed portion to said central compartment and a rupturable membrane sealably covering said opening, wherein said rupturable membrane can be ruptured to void any fluids from said recessed portion into said central compartment; and,
   c. wherein said housing comprises an open configuration wherein said side compartments are positioned on opposite sides of said shelf and a closed configuration wherein said side compartments are folded over said shelf so that said side compartment top edges are positioned over said central compartment top edge.

7. A medical procedure kit according to claim 6 including locking means for locking said kit in said closed configuration.

8. A medical procedure kit according to claim 7 wherein said shelf includes multiple wells for storing the medical supplies.

9. A medical procedure kit according to claim 8 wherein said central compartment includes at least one removable container and wherein at least one of said side compartments includes an opening for holding said at least one removable container.

10. A medical procedure kit according to claim 6 wherein said shelf includes at least one clip for releasably holding a catheter.

11. A medical procedure kit for performing a medical procedure comprising:
    an outer housing including a central compartment having a top edge defining a top opening and first and second side compartments hingedly connected to said central compartment, each of said side compartments having a top edge defining a top opening; and
    a shelf supported in said central compartment top opening for holding medical supplies for use during the medical procedure wherein said shelf includes a lip for engaging said top edge of said central compartment;
    wherein said housing comprises an open configuration wherein said side compartments are positioned on opposite sides of said shelf and a closed configuration wherein said side compartments are folded over said shelf so that said side compartment top edges are positioned over said central compartment top edge.

12. A medical procedure kit according to claim 11 wherein said lip lies in a first plane and wherein at least a portion of said shelf is inclined with respect to said first plane.

13. A medical procedure kit according to claim 12 wherein said shelf includes a drain hole for allowing waste fluids on said shelf to drain into said central compartment.

14. A combination kit and procedure tray for use in performing a medical procedure comprising:

a three-part outer shell including: a central portion having a bottom wall, front and rear walls, and first and second side walls, said front, rear and side walls each having an upper edge spaced apart from said bottom wall and defining a top opening into said central portion; a first side portion hingedly connected to said central portion first side wall; and a second side portion hingedly connected to said central portion second side wall, said first and second side portions each comprising a bottom wall, front and rear walls, and first and second side walls, said front, rear and side walls each having an upper edge spaced apart from said bottom wall and defining a top opening into said respective side portion;

a shelf including a top surface, an outer lip for sealingly engaging said front wall, rear wall, and first and second side walls of said central portion, a plurality of compartments extending through said top surface toward said bottom wall, each of said compartments including at least one side wall, a bottom wall spaced apart from said central portion bottom wall and a lip raised with respect to said top surface, and a drain opening through said top surface into said central portion, said shelf being inclined with respect to said central portion bottom wall and toward said drain opening;

wherein, said shelf includes at least one container removably supported in one of said compartments and at least one of said side compartments includes a holder for holding said at least one container;

at least one of said compartment bottom walls comprises a rupturable membrane; and, said first and second side portions being movable between a first configuration in which said top openings of said first and second side portions and said central portion lie generally in the same plane and a second configuration in which said front and rear top edges of said first and second side portions engage said front and rear portions of said central portion.

15. A combination kit and procedure tray according to claim 14 including substantially all of the equipment and supplies for performing a given medical procedure.

16. A combination kit and procedure tray according to claim 15 including at least one clip for holding a catheter and means for attaching said at least one clip to said tray.

17. A medical procedure kit comprising a procedure tray and a housing for supporting said procedure tray thereabove, wherein said procedure tray comprises a recessed compartment having an opening formed in the bottom thereof and a rupturable membrane sealably covering said opening, wherein said rupturable membrane can be ruptured to void any fluids from said compartment into said housing.

18. A medical procedure kit according to claim 17, further comprising a plug for sealing said opening after said membrane has been ruptured.

19. A medical procedure kit comprising:
   a. a container having an upper end, wherein said container has an absorbable material affixed inside said container to the bottom thereof; and
   b. a procedure tray sealably attached to the upper end of said container such that said container is completely closed, wherein said tray comprises a recessed compartment having an opening formed in the bottom thereof and a rupturable membrane sealably covering said opening, wherein said rupturable membrane can be ruptured to void any fluids from said compartment into said container, wherein the fluids are absorbed into said absorbable material.

20. A medical procedure kit according to claim 19, further comprising a plug for sealing said opening after said membrane has been ruptured.

* * * * *